(12) United States Patent
Numano et al.

(10) Patent No.: US 8,536,399 B2
(45) Date of Patent: Sep. 17, 2013

(54) METHOD OF REDUCING URINE ODOR AND ARTICLE FUNCTIONING TO REDUCE URINE ODOR

(75) Inventors: Kazuki Numano, Kagawa (JP); Kiy shi Miyazawa, Kagawa (JP); Takayuki Hisanaka, Kagawa (JP); Yozo Yamada, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 12/902,398

(22) Filed: Oct. 12, 2010

(65) Prior Publication Data

US 2011/0028925 A1 Feb. 3, 2011

Related U.S. Application Data

(62) Division of application No. 10/381,695, filed as application No. PCT/JP01/08339 on Sep. 26, 2001, now abandoned.

(30) Foreign Application Priority Data

Sep. 28, 2000 (JP) ................................ 2000-296622
May 8, 2001 (JP) ................................ 2001-137054

(51) Int. Cl.
*A61F 13/49* (2006.01)
*A61F 13/66* (2006.01)
*A61L 9/05* (2006.01)
*A61L 15/20* (2006.01)

(52) U.S. Cl.
USPC ...................... 604/359; 604/394; 604/385.27

(58) Field of Classification Search
None
See application file for complete search history.

(56) References Cited

U.S. PATENT DOCUMENTS

| | | |
|---|---|---|
| 3,890,242 A | 6/1975 | Curry |
| 3,920,020 A | 11/1975 | Kraskin |
| 5,603,927 A | 2/1997 | Kabushioki et al. |
| 5,610,208 A | 3/1997 | Dairoku et al. |
| 5,685,872 A | 11/1997 | Syverson |
| 5,797,893 A * | 8/1998 | Wada et al. ............ 604/372 |
| 6,933,420 B1 | 8/2005 | Corzani |

FOREIGN PATENT DOCUMENTS

| | | |
|---|---|---|
| EP | 0389023 | 9/1990 |
| EP | 0510619 | 10/1992 |
| EP | 0937467 | 8/1999 |
| EP | 0937467 A1 | 8/1999 |
| JP | 52-079028 | 7/1977 |
| JP | 53-004783 | 1/1978 |
| JP | 53-115821 | 10/1978 |
| JP | 02-180634 | 7/1990 |
| JP | 06-007418 | 1/1994 |
| JP | 06-030977 | 2/1994 |
| JP | 09-276380 | 10/1997 |
| JP | 11-158341 | 6/1999 |
| JP | 2001-104370 | 4/2001 |
| WO | 0000226 A | 1/2000 |

OTHER PUBLICATIONS

China Patent Office, Office Action, mailed Jul. 21, 2006.
Derwent Publication No. XP-002282775, Jul. 1982.
Derwent Publication No. XP-002282799, Sep. 1986.

* cited by examiner

*Primary Examiner* — Michael G Hartley
*Assistant Examiner* — Nabila Ebrahim
(74) *Attorney, Agent, or Firm* — Lowe Hauptman Ham & Berner, LLP

(57) ABSTRACT

The object of the present invention is to provide a method of reducing the odor of urine; and an article functioning to reduce the odor of urine. The present invention relates to the method comprising using a compound(s) reactive with aldehydes to thereby reduce the urine odor. Moreover, the present invention relates to the article, especially one for body fluid absorption, which functions to reduce the odor of urine by having compounds reactive with aldehydes to be present in absorption articles. As the compounds reactive with aldehydes, organic amines, organic amine salts, compounds producing organic amines by the reaction with discharges, organic amines, amide compounds, and compounds having a mercapto group can be used.

16 Claims, No Drawings

METHOD OF REDUCING URINE ODOR AND ARTICLE FUNCTIONING TO REDUCE URINE ODOR

CROSS REFERENCE TO RELATED APPLICATIONS

This application is a divisional application of U.S. application Ser. No. 10/381,695, which is the U.S. National Phase of PCT/JP01/08339, filed Sep. 26, 2001, which claims priority from Japanese Application Nos. 2000-296622, filed Sep. 28, 2000, and 2001-137054, filed May 8, 2001, each of which application is incorporated herein by reference in its entirety.

TECHNICAL FIELD

The present invention relates to a method of reducing urine odor and an article functioning to reduce urine odor. In particular, the present invention relates to a method of reducing urine odor in articles for body fluid absorption such as diapers and to an article for body fluid absorption functioning to reduce urine odor.

BACKGROUND ART

Articles for body fluid absorption such as paper diapers absorb discharges such as urine. Measures against an unpleasant odor during use of or at the time of disposing said body fluid absorption articles have been sought.

Many studies have conventionally been tried on the subject of reducing urine odor. Methods of using an absorbent such as a porous material, methods of using a bactericide, methods of neutralizing odor components with an acid or alkali, and the like have been proposed.

As the technology of utilizing physical adsorption, a number of methods such as a method of using zeolite (Japanese Patent Application Laid-open No. 49-23493/1974, Japanese Utility Model Application Laid-open 75318/1983, etc.), a method of using silica (Published Japanese Translation of PCT Application No. 512944/1999, etc.), a method of using both silica and zeolite (Published Japanese Translation of PCT Application No. 512946/1999, etc.), a method of using activated carbon (Japanese Utility Model Application Laid-open 165126/1982, etc.), and the like have been proposed.

However, methods of using physical adsorption by porous materials and the like have a certain limitation to the adsorption capacity. Occasionally, some adsorbents may reversibly release odor components and other adsorbents exhibit a slow deodorizing rate. In addition, the absorption capacity by pores cannot be effectively utilized in wet conditions immediately after the absorption materials have absorbed urine and the like. It is almost impossible to confirm the deodorizing effect in actual practice.

As attempts for adding a deodorizing function to articles for body fluid absorption such as sanitary napkin and paper diapers, Japanese Patent Application Laid-open No. 272050/1986 discloses an invention of incorporating ethyl alcohol into absorptive layers and Japanese Patent Application Laid-open No. 2345/1992 discloses an invention of incorporating a quaternary ammonium salt such as benzalkonium chloride.

In these inventions, based on the presumption that ammonia produced by decomposition of urea and amino acids in urine by microorganisms or enzymes possessed by the microorganisms is cause of urine odors, an antibacterial agent or a urea decomposition enzyme (urease) inhibitor is incorporated into an absorbing element to suppress ammonia production.

However, the inventors of the present invention have found that no ammonia odor is sensed when replacing a diaper and urine odor does not disappear even if an antibacterial agent is added to urine collected immediately after urination and that the methods of suppressing ammonia production and neutralizing ammonia cannot reduce the unpleasant sensation due to urine odor during wearing or replacing articles for body fluid absorption.

Other technologies that have been heretofore proposed with an objective of deodorizing articles for body fluid absorption such as diapers include a method of using a cation exchange fiber having a deodorizing effect (Japanese Patent Application Laid-open No. 212094/1993), a method of using a deodorizing component obtained from wood vinegar (Japanese Patent Application Laid-open No. 276330/1997), and the like. However, there are no practically effective countermeasures that can reduce unpleasant odors.

DISCLOSURE OF THE INVENTION

An object of the present invention is therefore to solve the above problems in the conventional technologies. A specific object of the present invention is to provide a method of reducing a urine odor without relying on a method of suppressing ammonia generation or a method of absorbing and neutralizing ammonia. Another object of the present invention is to provide an article having a function of reducing urine odor.

As a result of extensive studies to achieve the above objects, the present inventors have ascertained that ammonia is not a major cause of urine odor and that countermeasures against ammonia cannot provide a fundamental solution to the problem of the unpleasant urine odor. As a result of further studies, the present inventors have found that the compounds causing the urine odor are aldehydes and have searched for compounds exhibiting a deodorizing effect on aldehydes. As a result, the inventors have found that the urine odor can be reduced by using a compound(s) reactive with aldehydes. These findings have led to the completion of the present invention.

Specifically, the present invention relates to a method of reducing urine odor by using a compound(s) reactive with aldehydes and to an article possessing a function of reducing urine odor comprising a compound(s) reactive with aldehydes.

Moreover, the present invention also relates to a method of reducing urine odor and to an article possessing a function of reducing urine odor by using amines, organic amine salts, compounds producing organic amines by the reaction with discharges, amide compounds, or compounds having a mercapto group as a compound(s) reactive with aldehydes.

The present invention further relates to an article for body fluid absorption applied the above method of reducing urine odor. The article for body fluid absorption of the present invention comprises a liquid-permeable top sheet, an absorber which absorbs and retains body fluids, and a non-liquid-permeable back sheet. Preferably, a compound(s) reactive with aldehydes is (are) present in the back of the top sheet or in the upper layer of the absorber.

First, the present inventors have conducted studies to find if the conventional technologies for suppressing ammonia generation using an antibacterial agent can reduce a urine odor according to the following method.

1) 1 g of benzalkonium chloride or hexadecylpyridinium chloride was added to 100 g of urine collected from a healthy adult.

2) Urine obtained in 1) above was fed into a urine collection pad, a regular-type for women (manufactured by Uni-Charm Corp.) from the center of the pad.

3) The pad was put into a 1 little beaker, sealed with a food plastic wrap and an insulating tape, and allowed to stand for 2 hours at 37° C. The odors occurring were sensitively smelled and evaluated by the six-step odor emission rate indication method in Table 1.

TABLE 1

Six-step odor emission rate indication method

| Odor emission rate | Criteria |
|---|---|
| 0 | No odor |
| 1 | Barely sensed odor (Detectable threshold concentration) |
| 2 | Identifiable weak odor (Identifiable threshold concentration) |
| 3 | Easily sensed odor |
| 4 | Strong odor |
| 5 | Extremely strong odor |

The results are shown in Table 2.

TABLE 2

| Sample | Odor level |
|---|---|
| No addition (blank) | 4 |
| Benzalkonium chloride | 4 |
| Hexadecylpyridinium chloride | 4 |

The results of Table 2 show that no odor level difference was identified among the samples with the addition of an antibacterial agent, benzalkonium chloride or hexadecylpyridinium chloride, and the sample to which no antibacterial agent was added, confirming that the antibacterial agents have no urine odor reducing effect.

Next, the following experiment was carried out to identify the substance causing the unpleasant odor of urine.

1) Urine was collected from 6 male adults of 20-50 years old. The odorizing components were collected in a canister (stainless steel sampling vessel).

2) Peak analysis was carried out using micro-purge and trap-gas chromatograph/mass-spectrometry (MPT-GC/MS) to identify the compounds and calculate the concentrations from the area ratio of the compounds. The sample gases for the analysis of component concentrations using gas chromatograph/mass-spectrometry were collected twice, one immediately after urine collection and the other after storage for 24 hours at 40° C. The former was the sample gas for the analysis of the initial odor and the latter was the sample gas for the analysis of the heating odor.

3) A threshold value for human olfaction was examined by methods described in documents (for example, Recent deodorant and deodorizing technology, pp 118-125, published by Industry Technology Co., Ltd.) to numerically indicate the odor contribution ratio from the concentration of the component. Even if the actually detected concentration is low, a component with a low olfaction threshold value has a high contribution ratio to odor.

As a result, the initial odor contribution ratio was 33.8% for amines, 43.1% for aldehydes, 7.5% for sulfides, and 12.8% for hydrocarbons, whereas after storage for 24 hours at 40° C., the odor contribution ratio of heating odor was confirmed to be changed to 81.5% for aldehydes and 14.3% for sulfides.

The experimental results have made it clear that no urine deodorizing effect can be obtained as far as aldehydes gradually increasing after urination are not deodorized.

Based on the above experiments, the inventors of the present invention have confirmed that aldehydes must be reduced to reduce urine odor and attained the present invention which the urine odor is reduced using a compound(s) reactive with aldehydes.

The inventors have further searched for a compound(s) reactive with aldehydes and have discovered that organic amines, organic amine salts, compounds which form an organic amine when reacted with discharges (these compounds may be hereinafter referred to collectively as "organic amines"), amide compounds, and mercapto group-containing compounds are effective for reducing urine odor.

In the present invention, other assistant odor suppressors can be used together with the compounds reactive with aldehydes. As the other assistant odor suppressors, odor adsorption materials, water-soluble antibacterial agents, and neutralizing agents can be given. As the odor adsorption materials, any known odor adsorption materials such as zeolite, silica, activated carbon, and diatomaceous earth can be used. Among them, zeolite, activated carbon, and diatomaceous earth are particularly preferable. As water-soluble antibacterial agents, cetyl pyridinium chloride, zinc chloride, copper salts, copper ions, chlorohexidine, quaternary ammonium compounds, chelating agents, parabenes, chitins, and the like can be used.

An effective amount of pH buffering agent may also be added. Preferable pH buffering agents are organic acids such as citric acid, tartaric acid, succinic acid, and the like. Of these, tartaric acid is particularly preferable.

The present invention will be explained in more detail in the following description, which is not intended to be limiting of the present invention.

Aldehydes causing urine odor in the present invention are acetaldehyde, butanal (butylaldehyde), isobutanal, 2-methylbutanal, 3-methylbutanal, hexanal, and the like.

As examples of compounds reactive with these aldehydes, amino alcohols such as monoethanolamine, diethanolamine, and triethanolamine; organic amines such as dioctyl amine; organic amine salts such as ethanolamine hydrochloride and ethanolamine carbonate; compounds producing organic amines by reaction with discharges such as ethanolamine carboxylate and sulfonate; amides such as formamide, acetamide, propionamide, and butylamide; mercapto group-containing compounds such as thioalcohol; and the like can be given. Of these, diethanolamine, monoethanolamine, and acetamide are particularly preferable.

These compounds can be used either individually or in combination of two or more.

Aldehydes and compounds reactive with aldehydes are believed to react according to the following reaction mechanisms to deodorize the aldehydes causing the urine odor.

1) Reaction with a compound having an amino group

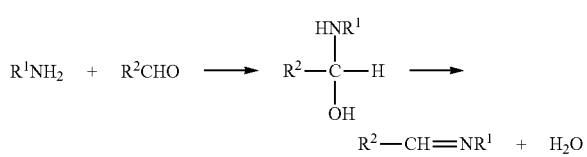

2) Reaction with a compound having a mercapto group

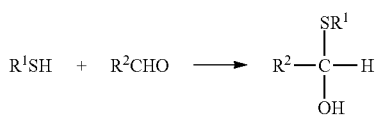

wherein $R^1$ and $R^2$ represent a hydrocarbon group.

Based on the above general reaction formulas, the reactions of 3-methylbutanal, acetaldehyde, or 2-methylbutanal with an organic amine, for example, are shown as follows.

1) Reaction with 3-methylbutanal

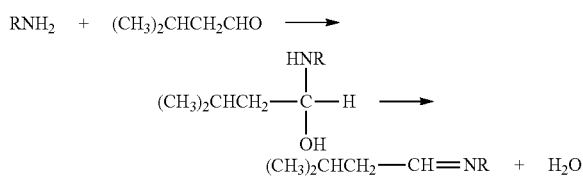

2) Reaction with acetaldehyde

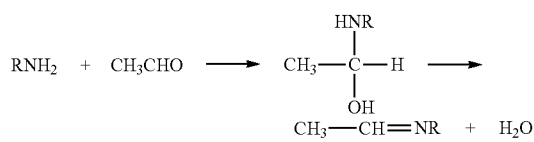

3) Reaction with 2-methylbutanal

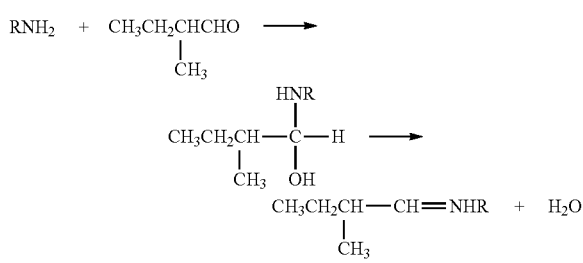

wherein R represents a hydrocarbon group.

Articles suitable for providing the urine odor reducing function by the presence of the compound(s) reactive with aldehydes include articles for body fluid absorption, shorts, underwear or clothes for infants or elderly persons, and the like.

As examples of the articles for body fluid absorption of the present invention, medical and sanitary goods such as sanitary napkins, panty liners, blood absorbers, as well as disposable diapers, incontinence pants, training pants, diaper holders, liners for cloth diapers, incontinence pads, urine-collection sheets, which are used for neonates, infants or elderly persons, and the like can be given.

The articles for body fluid absorption such as sanitary napkins, disposable diapers, and the like typically comprise a liquid-permeable surface material (top sheet), an absorber containing a water-absorption resin which absorbs and retains body fluids, and a back material with a non-liquid-permeable property (back sheet).

The disposable diaper may be either a panty-type diaper or an open-type diaper assembled for wearing using adhesive tape.

The top sheet for the absorptive article which directly contacts with the skin of the wearer must permit body fluids to permeate and must withstand 300 mm $H_2O$ or less water pressure according to the JIS L1092 (Test method for water resistance of textiles, water resistance test method A (low water pressure method)). The lower the water resistance, the higher the hydrophilic properties and the better the liquid permeability. A water resistance exceeding 300 mm $H_2O$ is unsuitable because the liquid permeability is so low that the material may allow fluids to flow onto the surface, resulting in leakage.

Currently available materials for such a top sheet include non-woven fabrics and porous films.

The non-woven fabrics used for the top sheet are not specifically limited, but those made of 1-5 d fiber with a nicking (Metsuke) of 10-50 $g/m^2$ are preferable. Dry methods and wet methods, such as a thermal bond method, span bond method, air laid method, chemical bond method, span lace method, and the like, are employed for the manufacture of non-woven fabrics. Top sheets for articles for body fluid absorption are mainly manufactured by a dry method in general. Thermal bond fabrics and span bond fabrics exhibiting well-balanced strength and texture are particularly preferable.

Fibers for non-woven fabric may be synthetic fibers such as polyolefin fibers (polyethylene, polypropyrene, etc.) and polyester fibers (polyethylene terephthalate, etc.), semi-synthetic fibers such as rayon, or natural fibers such as cotton, pulp, and silk.

As porous films, permeable porous films made from thermoplastics by extrusion, followed by boring using heated needles, embossing, hot blast, or the like can be used in the present invention.

Polyethylene (density: 0.86-1.1 $g/cm^3$), polypropylene (density: 0.89-1.2 $g/cm^3$), and the like can be used either individually or in combination as the thermoplastics for porous films. Multilayer porous films produced from a single thermoplastic or a combination of two or more kinds of thermoplastics may also be used.

The absorbers used in absorptive articles of the present invention are materials possessing capabilities of absorbing and retaining liquids, and include, but are not limited to, pulverized pulp, highly absorbent resins, tissue papers, and the like.

The constitution of the absorber can be appropriately changed corresponding to the required absorption performance and wearing sensation, which are affected by thickness and bending resistance.

There are no specific limitations to the back sheet used in the present invention so long as it is a non-liquid-permeable sheet-like material.

In addition to these components, a hydrophobic sheet may be provided at the end of the absorber to prevent leakage of liquids from the sides of the absorptive article. In the case of the absorptive article in the form of a pad, an adhesive for fixating with underwear and the like may be provided on the back sheet.

When a deodorant effective for reducing a urine odor is incorporated into the absorptive article of the present invention, the amount of addition is preferably from 0.002 g to 5 g per one sheet of the absorptive article. The density of the deodorant can be appropriately selected according to the kinds of the absorptive article. In the case of a urine absorption pad, for example, the density may be in the range of 0.01-20 $g/m^2$, and preferably 0.1-5 $g/m^2$. The density of deodorant in this range neither lowers the body fluid absorption performance of the absorptive article, nor impairs the safety of the article such as skin irritation. The above range, however, is not limitative since the amount of deodorant to be added varies depending on the shape of the article, the urine absorption amount during use, and the like.

The deodorant may be arranged in any position in which the deodorant comes into contact with urine, such as the top sheet, absorber, or back sheet. Preferable position is the back of the top sheet or the upper section of the absorber. This arrangement ensures the deodorizing effect is exhibited, since the deodorant is present in the route in which urine is absorbed at the time of urination.

In addition, because the deodorant is present in the passage of odor vaporized from the absorber when the absorptive article is replaced, contact between the odorous materials and the deodorant is ensured, resulting in exhibition of an excellent deodorizing effect.

If the deodorant is arranged on the surface of the top sheet, during wearing the deodorant is attached to the skin of the wearer before urination, thereby decreasing the probability of the deodorant coming into contact with urine. When the deodorant is arranged in the center or lower part of the absorber or in the back sheet, the probability of the deodorant coming into contact with urine is low if the amount of adsorbed urine is small. It is thus difficult for the odorant to exhibit an effect.

Inventions of high absorbent resins and moisture-permeable leakage-proof sheets (back sheet) have now made diapers wearable for a long time at night or during the time when the wearer is out of the home. In such articles worn for a long time, arranging the deodorant in the middle to lower part of the absorber or on the absorber side of the back sheet is particularly effective, because urine odor passes through micropores of the moisture-permeable leakage-proof sheets and is smelled. This, however, does not exclude arrangement of the deodorant on the surface or backside of the top sheet, in the upper, middle or lower part of the absorber, or on the absorbed side of the back sheet.

To further improve the deodorizing effect, the deodorant may be concentrated in locations near the urination area of the wearers, specifically, on the front side from the center in the absorptive article for men and around the center in the absorptive article for women.

The deodorant is preferably dissolved or dispersed in water and applied to the absorptive article.

In this instance, water-soluble polymers such as polyethylene glycol and polyvinyl alcohol, which are dissolved in urine, may be used as a binder. However, when applied onto the surfaces of non-woven fabrics and absorbers, particularly onto pulp surfaces, the water-soluble polymers may aggregate at the crossing points of the fibers after drying and increase the rigidity of the fibers, unpreferably resulting in an impaired texture.

Taking into account the absorption performance, the deodorant is preferably coated in the form of patterned dots, lines, or lattices. The method of patterning may be a method of masking the parts where the coating is unnecessary and spraying, a method of coating by extrusion using a slot coater, or a method of coating by transfer printing using a roll coater. In these methods, the deodorant bulk is preferably dissolved or dispersed in water without using a binder and applied to the absorptive article.

Although any coating methods can be employed, spray coating, extrusion coating using a slot coater, and a transfer coating using a roll coater are preferable.

Any coating patterns such as entire surface coating, dot coating, line coating, and lattice coating are applicable. When coating onto the top sheet and the upper parts of the absorber, dot coating, line coating, and lattice coating, in which uncoated parts are left after coating, are preferable rather than entire surface coating, which may impair transfer of discharges such as urine to the absorber.

BEST MODE FOR CARRYING OUT THE INVENTION

The present invention will now be described in more detail by way of examples and comparative examples, which should not be construed as limiting the present invention.

<Preparation of Absorptive Article>

EXAMPLE 1

An absorptive article was prepared as follows. 1) An absorptive article (Lifely urine-removing pad regular for women (manufactured by Uni-Charm Corp.)) comprising a liquid-permeable top sheet, an absorber made from pulp and a highly absorptive resin provided under the surface material and capable of absorbing and retaining body fluids, and a back sheet with non-liquid-permeable property was provided and the top sheet was peeled off. 2) Non-liquid-permeable films for the back sheet with a width of 1 cm were placed on the upper surface of the absorber at intervals of 1 cm. 3) An aqueous solution of diethanolamine and citric acid at concentrations to produce coating containing respectively 0.5 g/m$^2$ of diethanolamine and 3.0 g/m$^2$ of citric acid was prepared and sprayed on. 4) The coating was dried at 25° C. for 24 hours. 5) The peeled top sheet was returned to the original location on the absorptive article. Citric acid was added to control the pH and reduce problems such as skin roughness of the wearer.

EXAMPLES 2-6

Urine collection pads were prepared in the same manner as in Example 1 except that the deodorant compositions shown in Table 3 were sprayed onto the surface of the absorber.

Comparative Example 1

A urine collection pad was prepared in the same manner as in Example 1 except that nothing was applied to the surface of the absorber.

TABLE 3

| | Deodorant | | | | pH buffering agent | | Assistant odor suppressor |
|---|---|---|---|---|---|---|---|
| | DEA | MEA | DO | AA | CA | SA | Zeolite |
| Example 1 | 0.5 | 0.0 | 0.0 | 0.0 | 3.0 | 0.0 | 0.0 |
| Example 2 | 0.5 | 0.0 | 0.0 | 0.0 | 3.0 | 0.0 | 3.0 |
| Example 3 | 0.5 | 0.0 | 0.0 | 0.0 | 0.0 | 3.0 | 0.0 |
| Example 4 | 0.0 | 0.5 | 0.0 | 0.0 | 3.0 | 0.0 | 0.0 |
| Example 5 | 0.0 | 0.0 | 0.5 | 0.0 | 3.0 | 0.0 | 0.0 |
| Example 6 | 0.0 | 0.0 | 0.0 | 0.5 | 3.0 | 0.0 | 0.0 |
| Comparative Example 1 | 0.0 | 0.0 | 0.0 | 0.0 | 0.0 | 0.0 | 0.0 |

DEA: Diethanolamine; MEA: Monoethanolamine; DO: Dioctylamine; AA: Acetamide; CA: Citric acid; SA: Succinic acid Organoleptic Test (1) Urines were collected from four adult panelists immediately after uprising. The urines were mixed.

(2) 200 ml of the mixed urine obtained in (1) above was fed to the center of a urine collection pad described above.

(3) The urine collection pad into which the urine was fed in (2) above was put into a 1 L beaker. After sealing with a food wrap and an insulating tape, the beaker was allowed to stand for 24 hours at 37° C.

(4) After removing the food wrap from the beaker, the odor was organoleptically tested by four adult panelists A-D.

(5) The odors checked in the organoleptically test were indicated by the six-step odor emission rate indication method in Table 1 above.

<Results>

The results of the organoleptic test are shown in Table 4.

TABLE 4

|  | Panelist | | | | |
| --- | --- | --- | --- | --- | --- |
|  | A | B | C | D | Average |
| Example 1 | 2 | 1 | 1 | 1 | 1.25 |
| Example 2 | 1 | 0 | 1 | 1 | 0.75 |
| Example 3 | 1 | 2 | 2 | 1 | 1.50 |
| Example 4 | 1 | 1 | 2 | 2 | 1.50 |
| Example 5 | 2 | 2 | 2 | 1 | 1.75 |
| Example 6 | 1 | 1 | 2 | 1 | 1.25 |
| Comparative Example 1 | 4 | 3 | 4 | 4 | 3.75 |

From the comparison of Examples 1-6 and the Comparative Example 1, the unpleasant sensation of urine odor was confirmed to be reducible by having compounds reactive with aldehydes present in absorption articles.

INDUSTRIAL APPLICABILITY

As described above, urine odor was reduced in the present invention by using a compound(s) reactive with aldehydes. In addition, if the present invention is applied to articles such as a body fluid absorption article, the wearers themselves or persons assisting in the replacement of the articles for body fluid absorption feel the urine odor to a lesser extent, whereby it is possible to reduce the unpleasant sensation of urine odor from the absorptive article after urine absorption.

The invention claimed is:

1. Shorts, underwear or other clothes for infants or elderly persons, comprising:
   at least one portion having a multi-layer construction comprising:
   a water permeable top sheet,
   an absorber capable of absorbing and retaining body fluids and a back sheet with non-liquid permeable properties, and
   an aldehyde reactive odor attenuating compound coated on at least one of either the back side of the top sheet or the front of the absorber for reacting with aldehydes from a urine containing discharge wetting the water permeable top sheet and the absorber, and
   wherein the aldehyde reactive odor attenuating compound is chosen from monoethanolamine, diethanolamine, dioctyl amine, and acetamide.

2. Shorts, underwear or other clothes for infants or elderly persons, comprising:
   at least one portion having a multi-layer construction comprising:
   a water permeable top sheet,
   an absorber capable of absorbing and retaining body fluids and a back sheet with non-liquid permeable properties, and
   an aldehyde reactive odor attenuating compound coated on at least one of either the back side of the top sheet or the front of the absorber for reacting with aldehydes from a urine containing discharge wetting the water permeable top sheet and the absorber, and
   wherein the aldehyde reactive odor attenuating compound is chosen from monoethanolamine, diethanolamine, and acetamide.

3. The shorts, underwear or other clothes for infants or elderly persons of claim 2, wherein the at least one portion having a multi-layer construction further comprises a water impermeable back sheet.

4. The shorts, underwear or other clothes for infants or elderly persons of claim 2, wherein the aldehyde reactive odor attenuating compound is monoethanolamine.

5. The shorts, underwear or other clothes for infants or elderly persons of claim 2, wherein the aldehyde reactive odor attenuating compound is diethanolamine.

6. The shorts, underwear or other clothes for infants or elderly persons of claim 2, wherein the aldehyde reactive odor attenuating compound is acetamide.

7. The shorts, underwear or other clothes for infants or elderly persons of claim 2, further comprising a zeollite as an adsorption material.

8. The shorts, underwear or other clothes for infants or elderly persons of claim 2, wherein the aldehyde reactive odor attenuating compound is present in an amount ranging from 0.01 to 20 g/m$^2$.

9. The shorts, underwear or other clothes for infants or elderly persons of claim 1, wherein the aldehyde reactive odor attenuating compound is monoethanolamine.

10. The shorts, underwear or other clothes for infants or elderly persons of claim 1, wherein the aldehyde reactive odor attenuating compound is diethanolamine.

11. The shorts, underwear or other clothes for infants or elderly persons of claim 1, wherein the aldehyde reactive odor attenuating compound is acetamide.

12. The shorts, underwear or other clothes for infants or elderly persons of claim 1, wherein the aldehyde reactive odor attenuating compound is present in an amount ranging from 0.01 to 20 g/m$^2$.

13. The shorts, underwear or other clothes for infants or elderly persons of claim 1, wherein the aldehyde reactive odor attenuating compound is coated on the back side of the top sheet.

14. The shorts, underwear or other clothes for infants or elderly persons of claim 1, wherein the aldehyde reactive odor attenuating compound is coated on the front of the absorber.

15. The shorts, underwear or other clothes for infants or elderly persons of claim 2, wherein the aldehyde reactive odor attenuating compound is coated on the back side of the top sheet.

16. The shorts, underwear or other clothes for infants or elderly persons of claim 2, wherein the aldehyde reactive odor attenuating compound is coated on the front of the absorber.

* * * * *